US012702333B2

(12) United States Patent
Kiani et al.

(10) Patent No.: US 12,702,333 B2
(45) Date of Patent: Aug. 11, 2026

(54) ELECTRODE SYSTEMS FOR ELECTROCHEMICAL SENSORS

(71) Applicant: Willow Laboratories, Inc., Irvine, CA (US)

(72) Inventors: Massi Joe E. Kiani, Laguna Niguel, CA (US); Hung The Vo, Fountain Valley, CA (US); Kevin Hughes Pauley, Lake Forest, CA (US); Venkatramanan Krishnamani, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 583 days.

(21) Appl. No.: 18/050,377

(22) Filed: Oct. 27, 2022

(65) Prior Publication Data

US 2023/0135297 A1 May 4, 2023

Related U.S. Application Data

(60) Provisional application No. 63/263,277, filed on Oct. 29, 2021.

(51) Int. Cl.

*A61B 5/00* (2006.01)
*A61B 5/145* (2006.01)
*A61B 5/1477* (2006.01)
*G01N 27/30* (2006.01)
*G01N 27/327* (2006.01)

(52) U.S. Cl.

CPC ........ *A61B 5/1477* (2013.01); *A61B 5/14532* (2013.01); *G01N 27/301* (2013.01); *G01N 27/3275* (2013.01)

(58) Field of Classification Search

CPC ......................... A61B 5/1477; A61B 5/14532; G01N 27/301; G01N 27/3275

See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |

(Continued)

FOREIGN PATENT DOCUMENTS

WO WO 2023/077027 5/2023

OTHER PUBLICATIONS

US 2022/0192529 A1, 06/2022, Al-Ali et al. (withdrawn)

(Continued)

*Primary Examiner* — Adam Z Minchella

(74) *Attorney, Agent, or Firm* — KNOBBE, MARTENS, OLSON & BEAR, LLP

(57) ABSTRACT

An electrode system for an electrochemical sensor, such as a glucose sensor, is disclosed. The electrode system may include a working electrode, a reference electrode, and a counter electrode. The working electrode may comprise two layers of different metals, such as gold and platinum.

20 Claims, 10 Drawing Sheets

(56) References Cited

U.S. PATENT DOCUMENTS 5,436,499 A 7/1995 Namavar et al.
D361,840 S 8/1995 Savage et al.
D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,561,275 A 10/1996 Savage et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Ai-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin, IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab

(56) References Cited

U.S. PATENT DOCUMENTS

RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Ai-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.
D788,312 S 5/2017 Al-Ali et al.
9,649,054 B2 5/2017 Lamego et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.

(56) References Cited

U.S. PATENT DOCUMENTS 10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Ai-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Ai-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,542 B2 7/2022 Moein
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.

(56) References Cited

U.S. PATENT DOCUMENTS 11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Ai-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
12,538,084 B1 1/2026 Telfort et al.
12,539,046 B2 2/2026 Kiani
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0200538 A1* 8/2010 Petisce ................ B81C 1/00539 216/13
2010/0230285 A1* 9/2010 Hoss .................... A61B 5/1473 600/347
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0296672 A1 11/2013 O'Neil et al.
2013/0313130 A1 11/2013 Little
2013/0345921 A1 12/2013 Al-Ali et al.
2014/0038224 A1* 2/2014 Yu .......................... G01N 27/27 422/82.01
2014/0151225 A1* 6/2014 Yamashita ............. H01R 43/16 29/874
2014/0166076 A1 6/2014 Kiani et al.
2014/0180160 A1 6/2014 Brown et al.
2014/0187973 A1 7/2014 Brown et al.
2014/0262775 A1 9/2014 Papadimitrakopoulos et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2016/0196388 A1 7/2016 Lamego
2016/0367173 A1 12/2016 Dalvi et al.
2017/0024748 A1 1/2017 Haider

(56) References Cited

U.S. PATENT DOCUMENTS

2017/0173632 A1 6/2017 Ai-Ali
2017/0251974 A1 9/2017 Shreim et al.
2018/0242913 A1 8/2018 Zhu
2018/0242926 A1 8/2018 Muhsin et al.
2018/0247712 A1 8/2018 Muhsin et al.
2019/0008425 A1 1/2019 Srinivasan
2019/0239778 A1 8/2019 Srinivasan
2019/0239787 A1 8/2019 Pauley et al.
2019/0242010 A1* 8/2019 Srinivasan .......... C23C 14/0005
2019/0320906 A1 10/2019 Olsen
2019/0374713 A1 12/2019 Kiani et al.
2020/0060869 A1 2/2020 Telfort et al.
2020/0111552 A1 4/2020 Ahmed
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0069789 A1 3/2023 Koo et al.
2023/0080129 A1 3/2023 Garai
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0277101 A1 9/2023 Sliozberg et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Ai-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.
2025/0318761 A1 10/2025 Al-Ali et al.
2025/0322950 A1 10/2025 Al-Ali et al.
2025/0323417 A1 10/2025 Rey
2025/0329240 A1 10/2025 Kiani
2025/0344010 A1 11/2025 Al-Ali et al.
2026/0014333 A1 1/2026 Fernkvist et al.
2026/0014334 A1 1/2026 Danwihl
2026/0048198 A1 2/2026 Vo et al.

OTHER PUBLICATIONS

US 2024/0016391 A1, 01/2024, Lapotko et al. (withdrawn)

International Search Report and Written Opinion received in PCT Application No. PCT/US2022/078818 dated Feb. 3, 2023 in 12 pages.

Pundir et al., “Biosensing methods for determination of creatinine: A review”, Biosensors and Bioelectronics, vol. 126, Nov. 2018, pp. 707-724.

* cited by examiner

ELECTRODE SYSTEMS FOR ELECTROCHEMICAL SENSORS

CROSS REFERENCE TO RELATED APPLICATIONS

Any and all applications for which a foreign or domestic priority claim is identified in the Application Data Sheet as filed with the present application are hereby incorporated by reference under 37 CFR 1.57. For example, this application claims priority to U.S. Provisional Application No. 63/263,277, titled ELECTRODE SYSTEMS FOR ELECTROCHEMICAL SENSORS and filed on Oct. 29, 2021, the entire content of which is incorporated by reference herein in its entirety and for all purposes and forms a part of this specification.

FIELD OF THE DISCLOSURE

The present disclosure relates to physiological monitoring devices. More specifically, this disclosure relates to glucose monitoring devices and methods of making the same.

BACKGROUND

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system includes both a sensor to take glucose measurements from the interstitial space including blood and/or interstitial fluid of the patient and an insulin administration device which administers insulin to the patient based on the glucose measurements. Closed loop insulin administration systems allow individuals impacted by diabetes to go about daily life with much less worry about their insulin or glucose levels which can vastly improve a diabetic's quality of life.

SUMMARY

The present disclosure provides an electrode system for an electrochemical sensor. The electrode system can include a working electrode comprising a first layer comprising gold and a second layer comprising platinum; a reference electrode comprising silver; and a counter electrode comprising gold. The first layer comprising gold can have a thickness of about 2.5-3.5 μm, and the second layer comprising platinum can have a thickness of about 80-120 Å. The working electrode and the reference electrode can be positioned on one side of a substrate. The counter electrode can be positioned on an opposite side of the substrate relative to the working electrode and the reference electrode.

In some aspects, the electrochemical sensor can be a glucose sensor. In some aspects, the thickness of the first layer comprising gold can be about 3 μm. In some aspects, the thickness of the second layer comprising platinum can be about 100 Å. In some aspects, the reference electrode can have a thickness of about 2.5-3.5 μm. In some aspects, the counter electrode can have a thickness of about 2.5-3.5 μm. In some aspects, the reference electrode can have a thickness of about 2.5-3.5 μm. In some aspects, the substrate can comprise two base layers. In some aspects, at least one of the two base layers can comprise polyimide (PI), polyethylene (PE), or polyethylene terephthalate (PET).

In some aspects, the electrode system can further comprise a first polymer layer covering part of the working electrode and reference electrode. In some aspects, the first polymer layer can comprise polyimide (PI). In some aspects, the electrode system can further comprise a second polymer layer covering part of the counter electrode. In some aspects, the second polymer layer can comprise polyimide (PI).

In some aspects, a glucose sensor is provided. The glucose sensor can comprise an electrode system comprising a substrate; a working electrode positioned on one side of the substrate; a reference electrode positioned on the same side of the substrate as the working electrode; and a counter electrode positioned on an opposite side of the substrate relative to the working electrode and reference electrode. The working electrode can comprise a first gold layer and a second platinum layer. In some aspects, the first gold layer can have a thickness of about 2.5-3.5 μm. In some aspects, the second platinum layer can have a thickness of about 80-120 Å. In some aspects, the reference electrode can comprise silver. In some aspects, the counter electrode can comprise gold. In some aspects, the reference electrode can have a thickness of about 2.5-3.5 μm. In some aspects, the counter electrode can have a thickness of about 2.5-3.5 μm.

BRIEF DESCRIPTION OF THE DRAWINGS

Various aspects will be described hereinafter with reference to the accompanying drawings. These aspects are illustrated and described by example only, and are not intended to limit the scope of the disclosure. In the drawings, similar elements have similar reference numerals.

DETAILED DESCRIPTION

The present disclosure will now be described with reference to the accompanying figures, wherein like numerals refer to like elements throughout. The following description is merely illustrative in nature and is in no way intended to limit the disclosure, its application, or uses. Furthermore, the devices, systems, and/or methods disclosed herein can include several novel features, no single one of which is solely responsible for its desirable attributes or which is essential to practicing the devices, systems, and/or methods disclosed herein.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Definition

As used herein, common abbreviations are defined as follows:

° C. Temperature in degrees Centigrade
CE Counter electrode
RE Reference electrode
WE Working electrode
CGM Continuous glucose monitoring
DAN Diamino naphthalene
$GO_x$ Glucose oxidase
$H_2O_2$ Hydrogen peroxide Disclosed herein are electrode systems for an electrochemical sensor, for example, an analyte sensor, such as a glucose sensor. In some configurations, the analyte sensor may be integrated into a disease management system or other device configured to monitor a patient state and deliver medication on an ongoing or temporary basis. While reference may be made to a specific disease, such as diabetes, systems and methods described herein may be applicable to other diseases and conditions.

While in some examples, systems and methods described herein may reference monitoring or sensing of a specific parameter or blood analyte, such as glucose, other physiological conditions, physiological states, physiological parameters, physiological markers, blood analytes, the like or a combination thereof may be monitored or determined in addition or in the alternative to glucose. Similarly, while in some examples, reference may be made to a specific type of sensor, such as a glucose sensor, other analyte sensors may additionally or alternatively be used. For example, a glucose sensor may be configured to additionally measure other analytes. Additionally or alternatively, while reference may be made to specific types of invasive or non-invasive sensors, such as an invasive glucose sensor, any type of invasive or non-invasive sensor may be used, such as a non-invasive analyte sensor.

A. Example Disease Management System

Figure 1A:
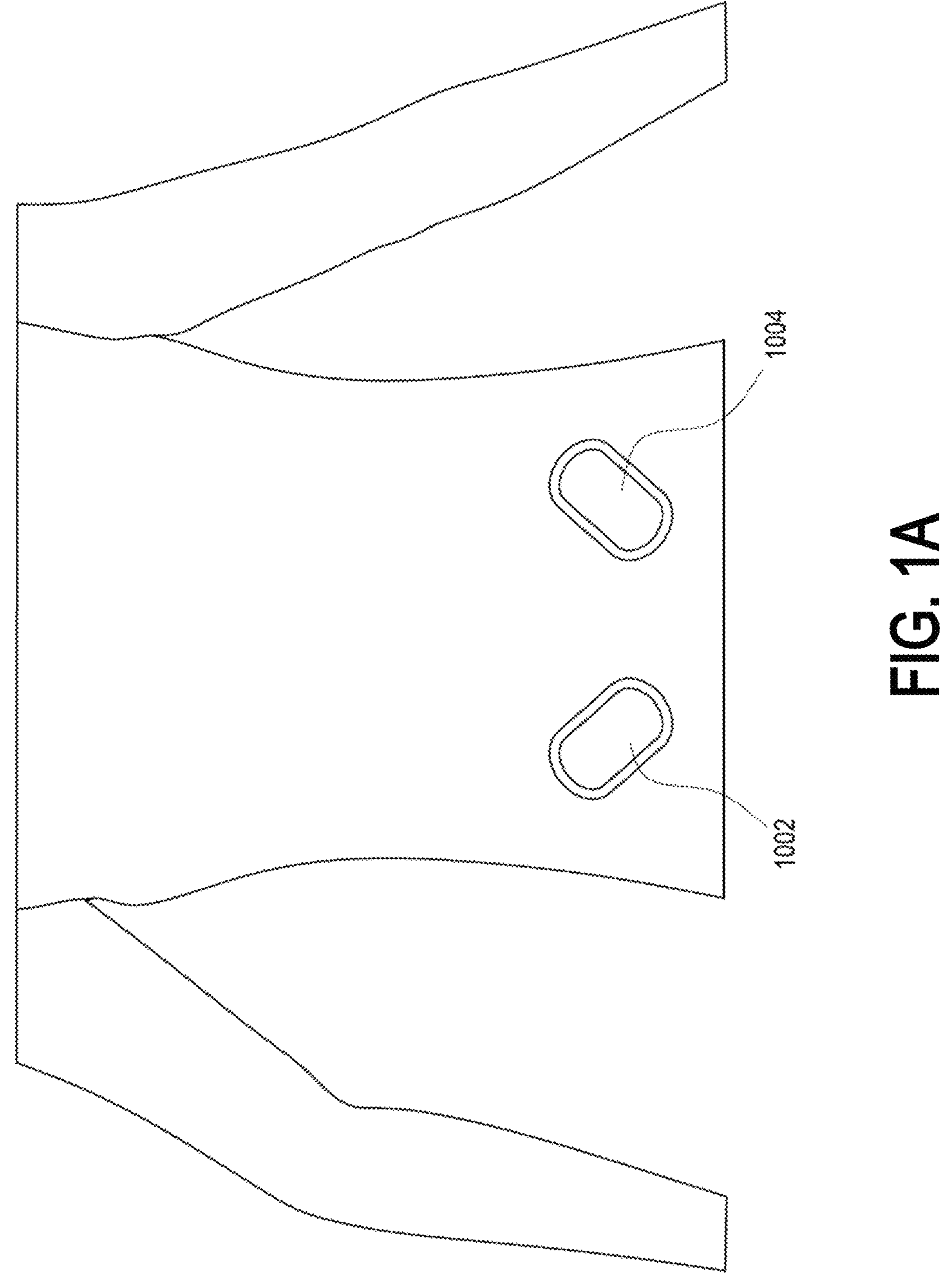
FIG. 1A illustrates a view of interleaved operation of insulin administration systems on a patient.

FIG. 1A illustrates a disease management system that may include one or more redundant disease management systems that may include standalone or combined glucose sensor and/or insulin administration systems. The disease management system may include a first disease management system 1002 and a second disease management system 1004.

Figure 1B:
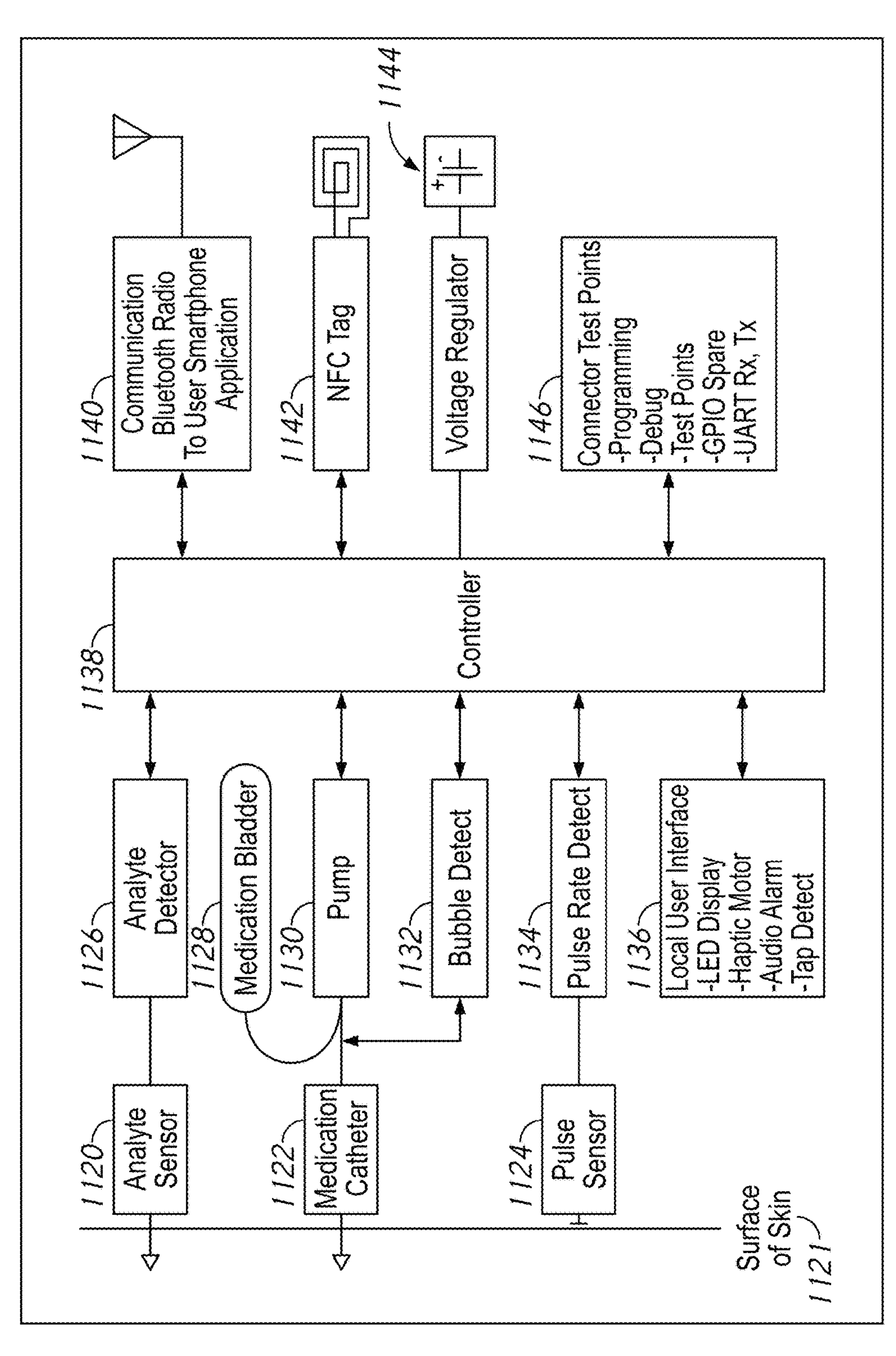
FIG. 1B illustrates an example disease management system that may be part of a disease management environment or used as an interleaved device.

FIG. 1B shows a block diagram of an example disease management system 1101. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud-based processor or user device.

As illustrated in FIG. 1B, a disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller. Other detailed description of the disease management system 1101 can be found in U.S. Patent Application Publication No. 2021/0236729 A1, which is incorporated here by reference in its entirety.

Figure 2:
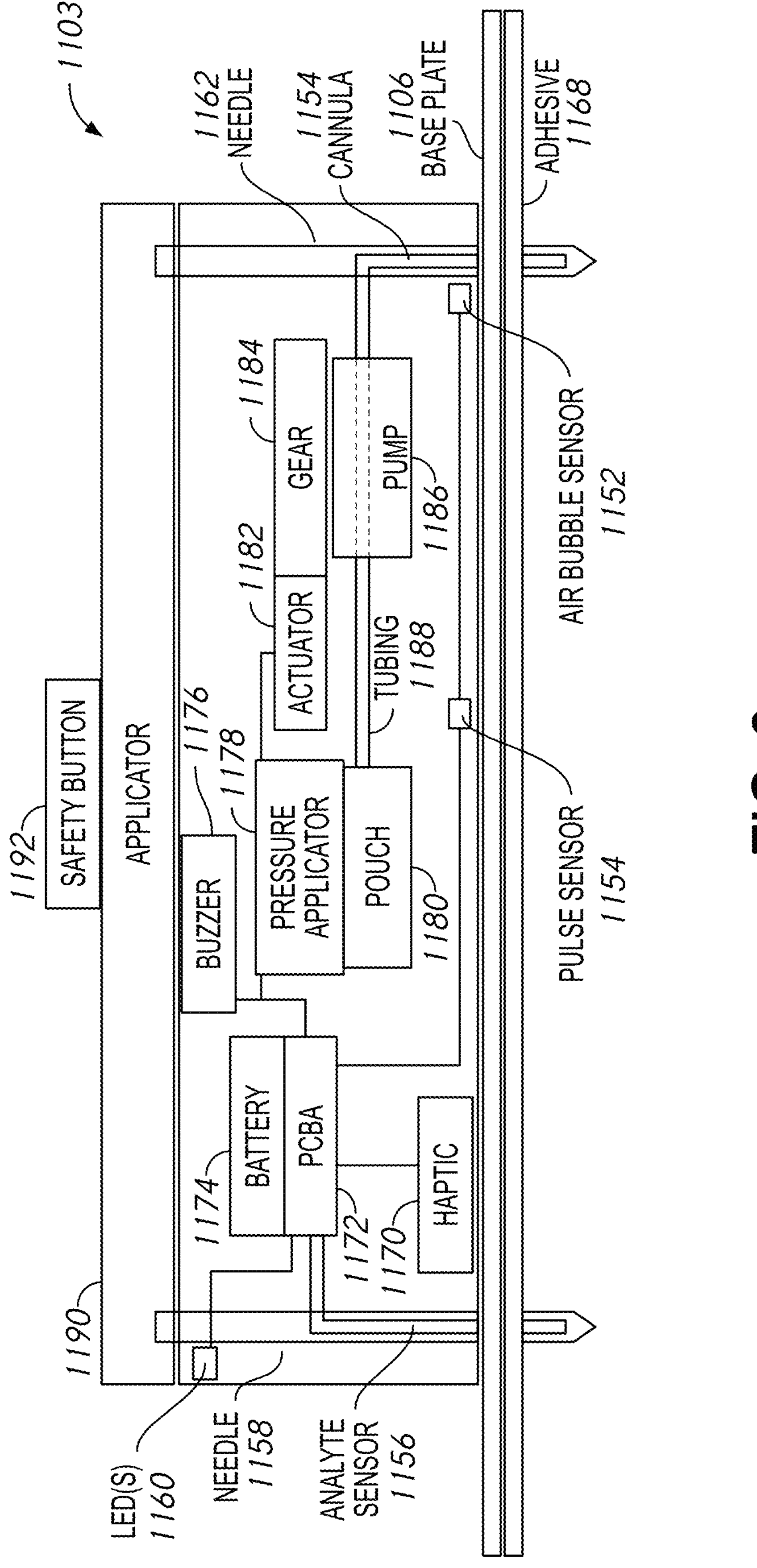
FIG. 2 illustrates an example implementation of a disease management system.

FIG. 2 illustrates an example implementation of a disease management system 1103 and applicator 1190 for applying a disease management system 1103 to a patient. In the illustrated example, an applicator 1190 may be configured to mate with the disease management system 1103. In some examples, a disease management system 1103 may include one or more needles 1158 that may include one or more analyte sensors (such as a glucose sensor) 1156. In some examples, the disease management system 1103 may include a base plate 1166 and an adhesive layer 1168 below the base plate 1166 to provide adhesion of the disease management system 1103 to the patient's skin. A housing of the disease management system 1103 may consist of a combination of flexible and rigid material so as to both provide support for the components of the disease management system 1103 and allow conforming, at least in part, of the disease management system 1103 to the skin of the patient.

Figure 3:
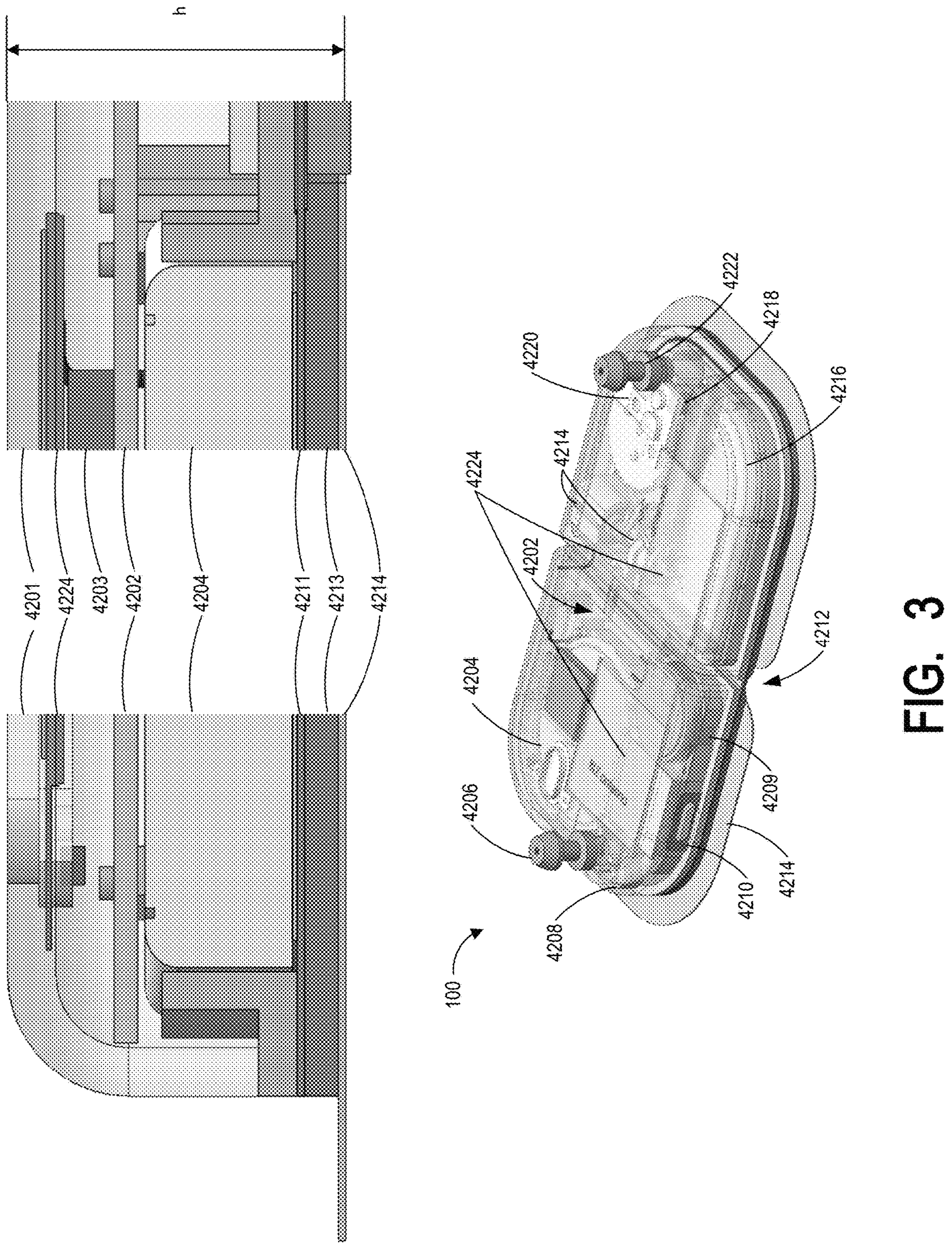
FIG. 3 illustrates an example layout of components of a disease management system.

In addition or in the alternative to one or more of the implementations described above, a disease management system may be combined into a compact design, such as illustrated in FIG. 3. FIG. 3 illustrates cross sectional and perspective views of an example embodiment of a disease management system 100. The disease management system 100 can include a combined glucose monitor and insulin pump. As illustrated by FIG. 3, a disease management system 100 can include a battery 4204, a PCBA 4202, an analyte sensor and needle mount 4206, an adhesive latch mechanism 4208, a buzzer 4210 and water resistant film or layer, a vibration motor 4209, a medication pouch assembly 4216, a pouch puncture assembly 4214, one or more light pipes 4218, a cannula and needle 4222, and a pump assembly 4220.

Figure 4:
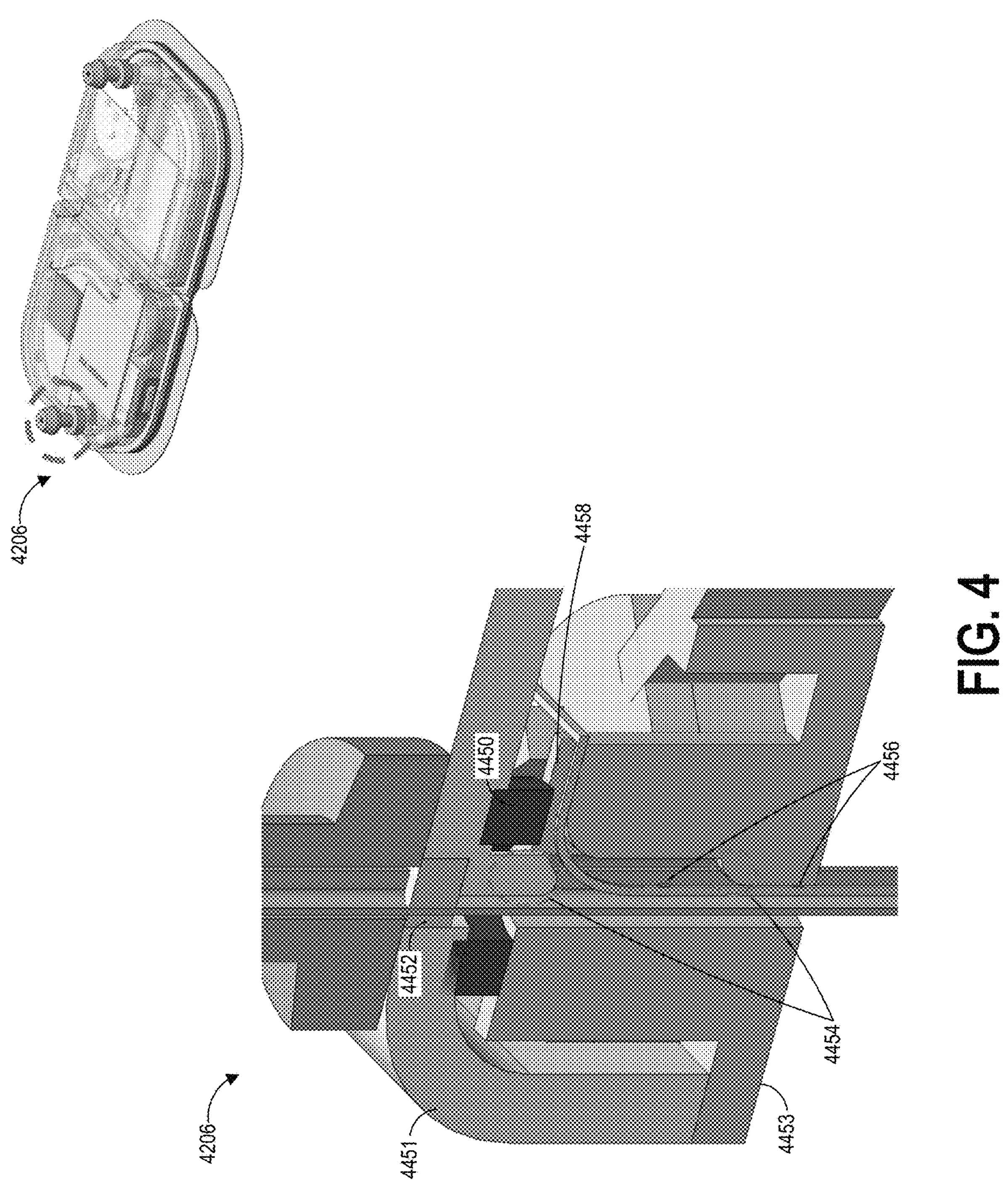
FIG. 4 illustrates an example analyte sensor seal and mount for an implementation of a disease management system.

FIG. 4 illustrates an example analyte sensor and mount 4206 of a disease management system. In some examples, an analyte sensor and needle mount 4206 can include a gasket 4450. The gasket can be configured to seal the sensor from external fluids that may otherwise flow into the disease management system. In some examples, an analyte sensor and needle mount 4206 may include features to position the analyte sensor and needle properly. For example, an analyte sensor and needle mount 4206 may include portions 4454 configured to position the sensor properly so as to avoid upward shift of the sensor before, during, or after insertion. In some examples, one or more of a needle and sensor can include dimples 4456 or other positioning features to help prevent a sensor from touching the needle and being damages when the needle is withdrawn.

B. Example Electrode System for Electrochemical Sensors

An analyte sensor, such as a glucose sensor is an amperometric electrochemical biosensor generating a current from the electrochemical reaction between glucose and a glucose oxidase layer on a working electrode (WE). The reference electrode (RE) eliminates the potential arising from the solution medium. The counter electrode (CE) acts as a reference half-cell to supply the required current for the electrochemical reaction, whereas the WE acts as a sensing half-cell to produce the current. The glucose monitoring device described herein comprises at least two electrodes—the working electrode and the reference electrode.

Figure 5A:
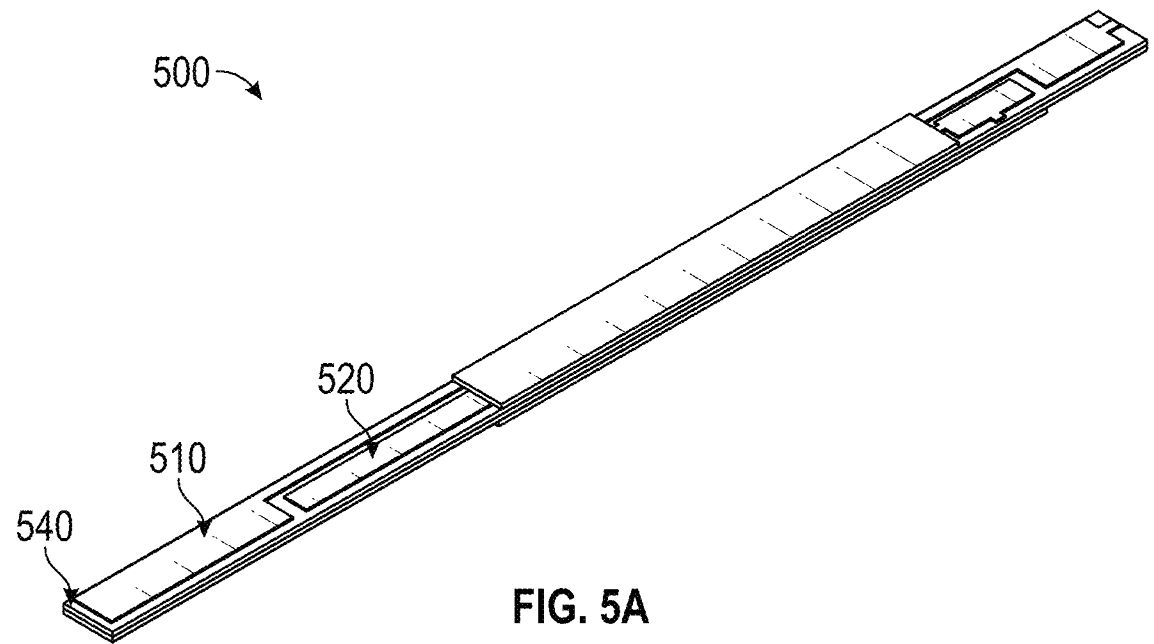
FIG. 5A-5C illustrate different views of an example electrode system for an analyte sensor.
Figure 5B:
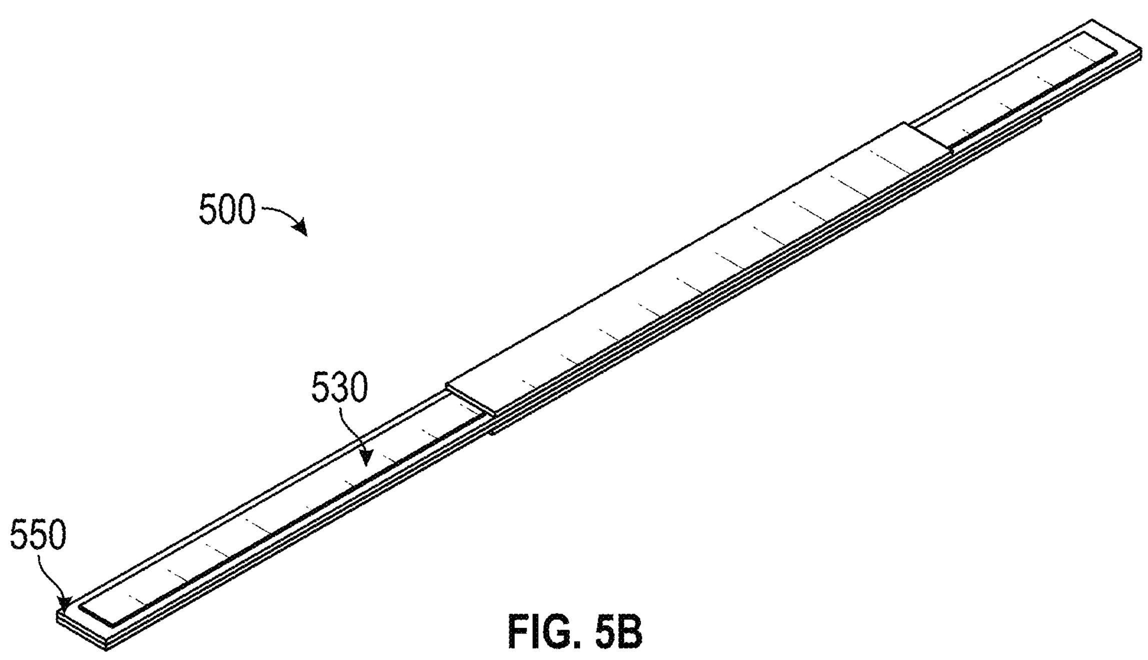
Figure 5C:
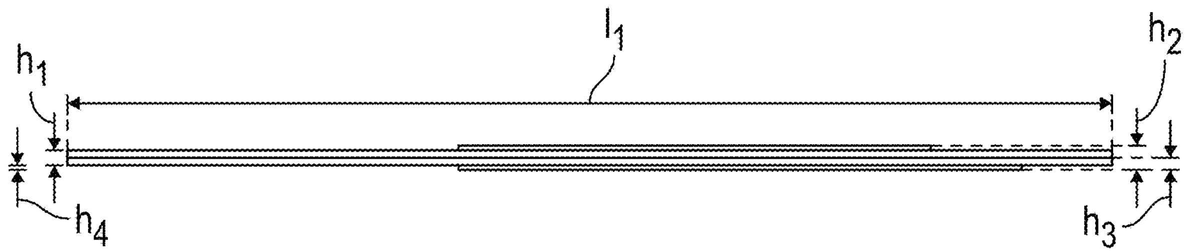

FIGS. 5A-5C illustrate different views of an example electrode system 500 comprising a working electrode 510, reference electrode 520 and a counter electrode 530. FIG. 5A shows a working electrode 510 and a reference electrode 520 on one side of the substrate. FIG. 5B shows a counter electrode 530 on the other side of the substrate. FIG. 5C illustrates the side view of the example electrode system 500, as well as the sizes and thickness of different layers. As a non-limiting example, the length of an example electrode system $l_1$ may be about 8 mm, the thickness of layers 540 and 550 $h_1$ may be about 120 μm, the thickness of all the layers $h_2$ may be about 170 μm, the thickness $h_3$ of layers 550, 530 and 570 $h_3$ may be about 60 μm, the thickness of layer 570 $h_4$ may be about 20 μm.

To address the comfort of a user having to use a sensor device, the reduction in size (diameter) of sensor electrodes is important, as is the durability of the probe design to withstand the rigors of a physically active patient and importance of repeatable accuracy and economical production of these probes to keep CGM unit costs reasonable for typical patients. Systems and methods described herein help address the above concerns.

Advantageously, placing the working electrode and reference electrode on the opposite side of the substrate relative to the counter electrode can help downsize the glucose sensor comparing to placing all three electrodes on one side of the substrate, which is important for a user's comfort. For example, if the glucose sensor is placed in a needle to be inserted into a patient's body such as in a wearable device like the disease management system 1103, the size of the glucose sensor may partially determine the diameter of the needle and a miniaturized sensor may help alleviate the patient's pain and improve the comfort level, especially when the patient needs to wear the device for relatively long time.

Figure 5D:
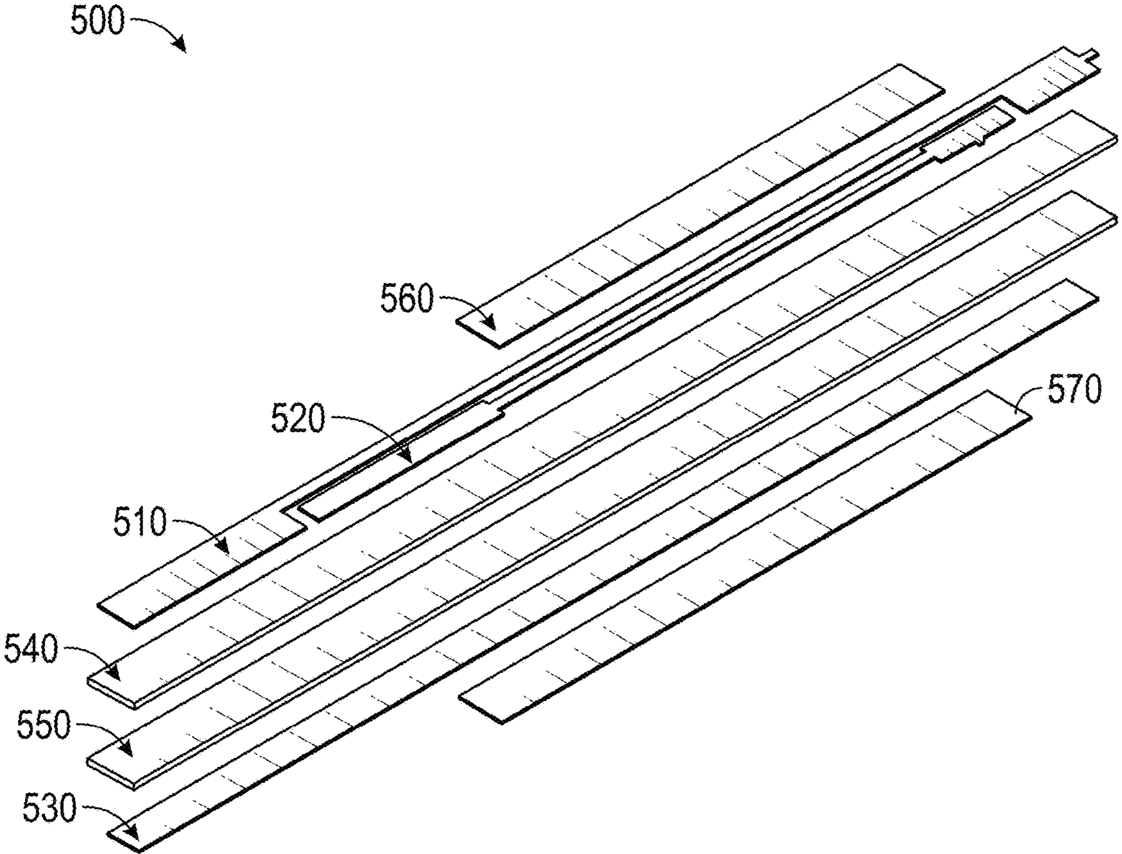
FIG. 5D illustrates different layers of an example electrode system for an analyte sensor.

FIG. 5D illustrates different layers in an example electrode system 500. As shown in FIG. 5D, the electrode system 500 may comprise a first polymer layer 560, a working electrode 510, a reference electrode 520, a second polymer layer 540, a third polymer layer 550, a counter electrode 530, and a fourth polymer layer 570.

In some aspects, the thickness of the first polymer layer 560 is about 10-30 μm, about 15-25 μm, about 15 μm, about 20 μm, about 25 μm, about 30 μm, or any other thickness. In some aspects, the first polymer layer 560 may comprise polyimide (PI) or other equivalent polymer.

In some aspects, the working electrode 510 and/or the reference electrode 520 may comprise one or more metals. In some further aspects, the working electrode 510 and/or the reference electrode 520 may comprise platinum (Pt), gold (Au), silver (Ag), rhodium (Rh), iridium (Jr), or combinations thereof.

In one aspect, the working electrode 510 may comprise Pt. In some aspects, the working electrode 510 may comprise both Pt and Au. In another aspect, the working electrode 510 comprises both Pt and Ir. In some aspects, the working electrode 510 may comprise two different metal layers. In some aspects, the bottom metal layer of a working electrode 510 may be Au and the top metal layer of the working electrode 510 may be Pt. In some aspects, the thickness of the bottom metal layer may be about 2-4 μm, about 2.5-3.5 μm, about 2 μm, about 2.5 μm, about 3 μm, about 3.5 μm, about 4 μm, or any other thickness. In some aspects, the thickness of the top metal layer may be about 50-150 Å, about 80-120 Å, about 50 Å, about 70 Å, about 90 Å, about 100 Å, about 120 Å, about 150 Å, or any other thickness. In some aspects, the thickness of the top metal layer may be much less than the thickness of the bottom metal layer. The ratio of the thickness of the top metal layer to the thickness of the bottom metal layer may be less than about 1/500, 1/300, 1/100, or less than any other ratio. Such a two-layer working electrode configuration can provide a platinum electrode surface for glucose detection and other better qualities such as higher electrical conductivity comparing to a pure platinum electrode. It might also cost less to manufacture this two-layer electrode comparing to manufacturing a pure platinum electrode.

In some aspects, the reference electrode 520 may comprise silver. In some aspects, the thickness of the reference electrode in the reference electrode may be about 2-4 μm, about 2.5-3.5 μm, about 2.5 μm, about 3 μm, about 3.5 μm, about 4 μm, or any other thickness. In some aspects, the thickness of the working electrode 510 and the reference electrode 520 may be similar. In another aspect, the reference electrode may comprise silver and silver chloride (Ag/AgCl).

Figures 6A, 6B:
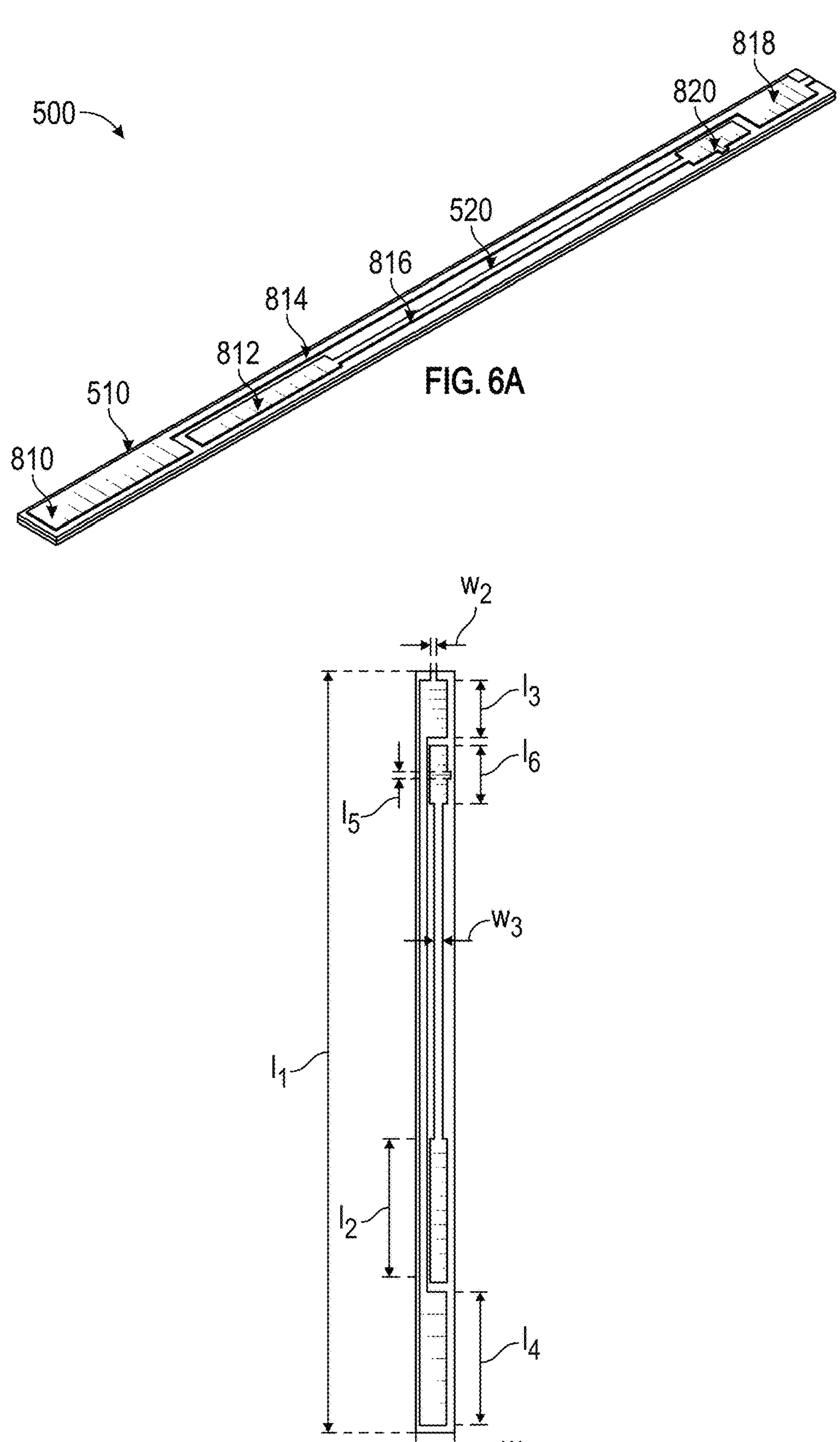
FIG. 6A show the working electrode and reference electrode in an example electrode system.
FIG. 6B illustrates the dimensions of the working electrode and reference electrode in an example electrode system.

FIG. 6A shows the working electrode 510 and reference electrode 520 in the example electrode system 500. In some aspects, the reference electrode 520 may comprise an electrode part 812, a connector part 820, and a wire part 816 connecting the electrode part 812 and the connector part 820. In some aspects, the connector part 820 may be used to connect to the electrical circuits of the system. In some aspects, the width of the wire part 816 $w_3$ may be about 0.06-0.12 mm, about 0.06-0.10 mm, about 0.06 mm, 0.08 mm, 0.10 mm, 0.12 mm, or any other width. In some aspects, the length of the wire part 816 is about 6.5-7.4 mm, about 6.5 mm-7.0 mm, about 6.5 mm, 6.8 mm, 7.1 mm, 7.4 mm, or any other length. In some aspects, the connector part 820 and the electrode part 812 may be asymmetric. In some aspects, the width of the connector part 820 may be about 0.24-0.36 mm, about 0.28-0.32 mm, about 0.24 mm, about 0.30 mm, about 0.36 mm, or any other width. In some aspects, the length of the connector part 820 $l_6$ may be about 0.5-0.7 mm, about 0.5 mm, about 0.6 mm, about 0.7 mm, or any other length. In some aspects, the length of the electrode part 812 $l_2$ may be about 1.4-1.6 mm, about 1.4 mm, about 1.5 mm, about 1.6 mm, or any other length. In some aspects, the reference electrode 520 may have other shapes.

With continued reference to FIG. 6A, in some aspects, the working electrode 510 may comprise an electrode part 810, a connector part 818, and a wire part 814 connecting the electrode part 810 and the connector part 818. In some aspects, the connector part 818 may be used to connect to the electrical circuits of the system. In some aspects, the working electrode 510 may be arranged to encompass the reference electrode 520 without contacting the reference electrode 520. In some aspects, the length of the wire part 814 may be about 8.5-9.5 mm, about 8.5 mm, about 9.0 mm, about 9.5 mm, or any other length. In some aspects, the length of the electrode part 810 $l_4$ may be about 1.3-1.5 mm, about 1.3 mm, about 1.4 mm, about 1.5 mm, or any other length. In some aspects, the length of the connector part 818 $l_3$ may be about 0.5-0.7 mm, about 0.5 mm, about 0.6 mm, about 0.7 mm, or any other length. In some aspects, the working electrode 510 may comprise other shapes.

FIG. 6B illustrates the dimensions of a working electrode 510 and a reference electrode 520 in an example electrode system. As a non-limiting example, the length of the electrode part 812 $l_2$ is about 1.5 mm, the length of the connector part 818 $l_3$ is about 0.6 mm, the length of the electrode part 810 $l_4$ is about 1.4 mm, the length $l_5$ is about 0.06, the length $l_6$ is about 0.6 mm, the width of the electrode system $w_1$ is about 0.36 mm, the width $w_2$ is about 0.06 mm, the width $w_3$ is about 0.08 mm.

Figures 7A, 7B:
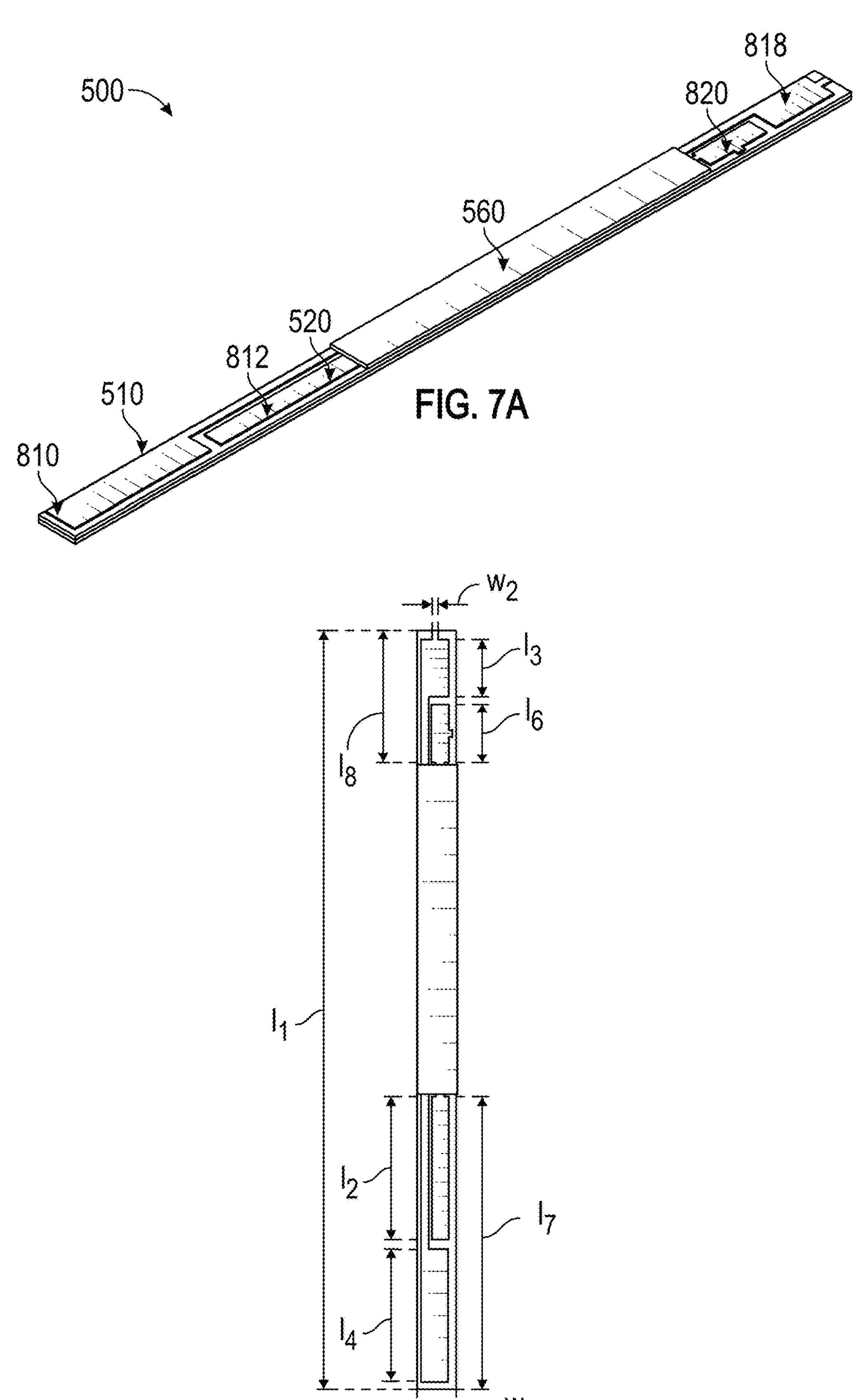
FIG. 7A show the working electrode and reference electrode partly covered by a polymer layer in an example electrode system
FIG. 7B illustrates the dimensions of the working electrode and reference electrode partly covered by a polymer layer in an example electrode system.

FIG. 7A illustrates a plan view of an example electrode system 500 viewed from the side of first polymer layer 560 and the dimensions. In some aspects, the first polymer layer 560 may cover the wire parts 814 and 816 of the working electrode 510 and reference electrode 520 respectively. In some aspects, the length of first polymer layer 560 may be about 3.5-3.9 mm, about 3.5 mm, about 3.7 mm, about 3.9 mm, or any other lengths. The first polymer layer 560 may provide protection of the electrodes.

FIG. 7B illustrates the dimensions of the first polymer layer 560 in an example electrode system. As a non-limiting example, the length $l_8$ is about 1.4 mm, the length $l_7$ is about 3 mm.

Referring back to FIG. 5D, in some aspects, the thickness of the second polymer layer 540 is about 50-70 μm, about 55-65 μm, about 50 μm, about 55 μm, about 60 μm, about 65 μm, or any other thickness. In some aspects, the second polymer layer 540 may comprise polyimide (PI), polyethylene (PE), polyethylene terephthalate (PET), or other equivalent polymer.

With continued reference to FIG. 5D, in some aspects, the thickness of the third polymer layer 550 is about 50-70 μm, about 55-65 μm, about 50 μm, about 55 μm, about 60 μm, about 65 μm, or any other thickness. In some aspects, the third polymer layer 550 may comprise polyimide (PI), polyethylene (PE), polyethylene terephthalate (PET), or other equivalent polymer. In some aspects, the thickness of the second and third polymer layer may be similar. In some aspects, the second and third polymer layer may serve as the substrate together. In some aspects, the second and third polymer layer may be combined as one single layer, and the thickness of this single layer maybe the sum of the thickness of the second and third polymer layer. In some aspects, the third polymer layer may be omitted from the electrode system.

With continued reference to FIG. 5D, the counter electrode 530 may comprise one or more metals described herein. In one aspect, the counter electrode comprises gold. In some aspects, the thickness of the counter electrode 530 may be about 2-4 μm, about 2.5-3.5 μm, about 2 μm, about 2.5 μm, about 3 μm, about 3.5 μm, about 4 μm, and or other thickness. In some aspects, the counter electrode 530 may be omitted from the electrode system.

With continued reference to FIG. 5D, in some aspects, the thickness of the fourth polymer layer 570 may be about 15-30 μm, about 25-35 μm, about 15 μm, about 20 μm, about 25 μm, about 30 μm, or any other thickness. In some aspects, the fourth polymer layer 570 may comprise polyimide (PI) or other equivalent polymer.

Figure 8A:
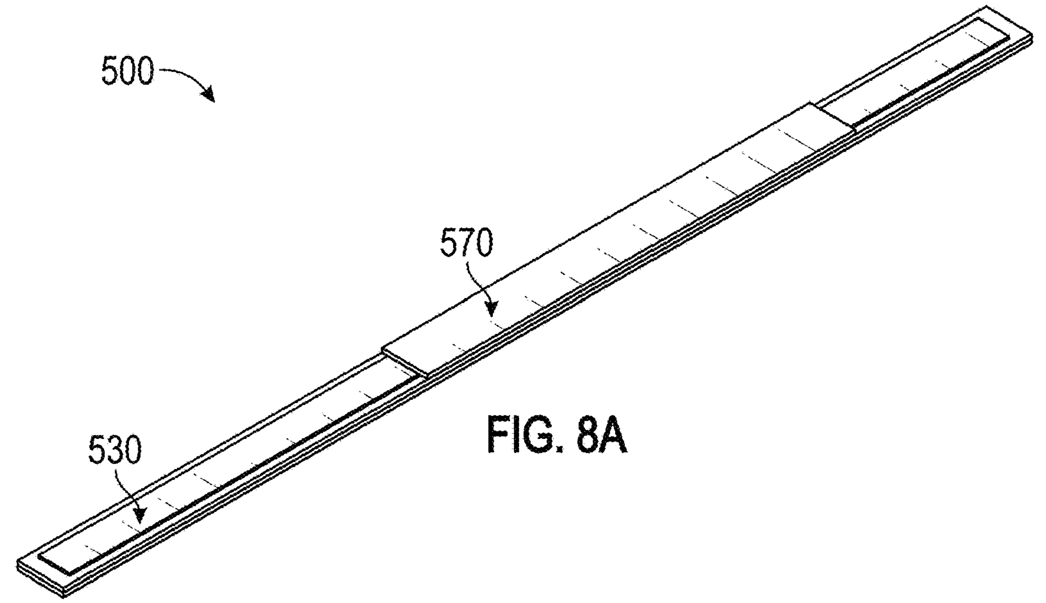
FIG. 8A show the counter electrode partly covered by a polymer layer in an example electrode system.

FIG. 8A illustrates a plan view of an example electrode system viewed from the side of fourth polymer layer 570 and the counter electrode 530. As shown in FIG. 8A, in some aspects, the counter electrode 530 may comprise a rectangular shape. In some aspects, the length of the rectangular shape may be about 7-10 mm, about 7 mm, about 8 mm, about 9 mm, about 10 mm, or any other length. In some aspects, the width of the rectangular shape $w_4$ may be about 0.2-0.36 mm, about 0.20 mm, 0.26 mm, 0.3 mm, 0.36 mm, or any other width. In some aspects, the fourth polymer layer 570 can cover part of the counter electrode 530. In some aspects, the length of the fourth polymer layer 570 may be about 4.0-4.9 mm, about 4.0-4.5 mm, about 4.0 mm, about 4.3 mm, about 4.6 mm, or any other length. The fourth polymer layer 570 may provide protection of the counter electrode.

Figure 8B:
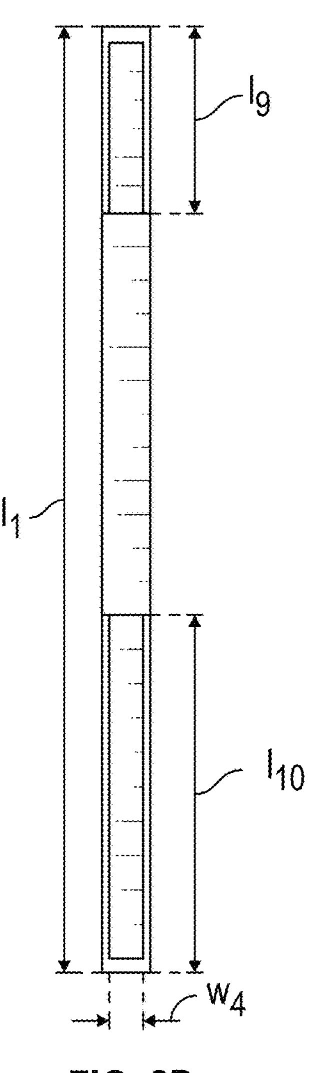
FIG. 8B illustrates the dimensions of the counter electrode partly covered by a polymer layer in an example electrode system.

FIG. 8B illustrates the dimensions of fourth polymer layer 570 and the counter electrode 530. As an non-limiting example, the width of the counter electrode 530 $w_4$ is about 0.26 mm, the length $l_9$ is about 0.7, the length $l_{10}$ is about 3 mm.

C. Surface Characteristics of Example Electrode System

The surface characteristics of working electrodes are important for all subsequent steps of fabrication of the CGM sensor. Any deposits of organic material, chemical impurities and oxidized metal can lead to irregular electrical conductivity along the surface due to different surface adsorption characteristics towards the analyte (for electrochemical deposition, electro-polymerization, electrochemical area determinations, etc.); irregular physical adsorption of inner selective layers (PoPD, cellulose acetate, Nafion™, polyphenol etc.); or irregularities in distribution of the hydroxyl groups on the Pt wire surface, which is critical for uniform oxidation rates of $H_2O_2$. There are various protocols of cleaning the surface of working electrodes, including but not limited to: a) mechanical agitation in 100% acetone and deionized water using titanium-tip sonication; b) soaking in concentrated nitric acid to dissolve residual organic matter and to etch the platinum surface slightly; and c) electrochemical conditioning/activation of the surface by performing multiple cycles of cyclic voltammetry between −0.2 [V] to 1.145 [V] in 1 M sulfuric acid ($H_2SO_4$).

Therefore, the electrochemical oxidation reactions of most redox species are preferred at potentials close to those of the platinum oxide (Pt(O)) surface formation for greatest response.

Electrochemical species undergo electrocatalytic oxidation at the Pt surface through the reaction with oxygen, which may come from bulk water or from surface oxides on the electrode formed by anodic activation of the Pt surface. Having the oxide layer on the Pt surface accelerates the electrochemical charge transfer reactions because of readily available platinum oxide. In the first step of this cyclic mechanism, $H_2O_2$ reacts with the surface of Pt to form Pt(O), releasing one molecule of $H_2O$. In the second step, a second molecule of $H_2O_2$ reduces Pt(O) to metallic Pt, releasing a second molecule of second $H_2O$ and $O_2$. The first reaction is a rate-limiting step in this two-part reaction. Incorporating Pt(O) at the surface (activation) exhibit a faster rate of $H_2O_2$ decomposition because the rate limiting step of the reaction is skipped in the first cycle.

There are many potential parallel/competing Pt based $H_2O_2$ electrochemical oxidation reaction mechanisms. The anodic activation of Pt can be achieved by application of cyclic voltammetry, where the electrode is anodized by scanning the potential in the anodic region and/or holding the potential for some time at the anodic limit. In one example, during Pt cleaning procedure with 1 M $H_2SO_4$, the cyclic voltammetry scans were stopped at the final high anodic potential of 1.145 V vs Ag/AgCl. At this potential a uniform Pt(O) layer and an activated working electrode surface is formed.

To detect $H_2O_2$, GOx enzymatic layer will be deposited on the platinum electrode, along with other layers for normalizing the glucose signal, which will act as the working electrode (WE). A three-electrode configuration includes two other electrodes; a solid-state silver/silver chloride (Ag/AgCl) as a reference electrode (RE) against which the potential of the working electrode is maintained at a constant value; and a counter electrode (CE) made of any stable/noble metal (Au, Pt, stainless steel or others) which acts as a conduit to pass the current between the working electrode and itself. When the working electrode surface is held at the operating potential of the CGM (+0.6V) with respect to Ag/AgCl, $H_2O_2$ oxidizes to $O_2$ and releases two electrons per molecule of $H_2O_2$.

$$2AgCl+2e^- \rightarrow 2Ag+2Cl^-$$

However, at this potential other endogenous redox active species such as ascorbic acid, uric acid as well as exogenous redox active species such as acetaminophen also undergo reduction/oxidation at the electrode surface. This can lead to an increase or decrease in the amperometric signal. As described herein, the incorporation of a second permeability-layer and/or an oxygen-replenishing layer can substantially reduce or eliminate the signal caused by the interference by blocking these interfering species from reaching the electrode surface. As described herein, CGM sensor interference can be reduced/eliminated by adding a combination of enzymes that specifically catalyze the decomposition of the following interfering molecules in the outer layers of the sensor before they reach the electrode: ascorbic acid, uric acid, or acetaminophen, hydroxyurea, cholesterol, creatinine, dopamine, ethylenediaminetetraacedic acid (EDTA), gentisic acid, heparin, or salicylic acid, or combinations thereof. The enzymes specific for each of the interfering molecules may be add to one or more of the second-permeability selective layer (inner selective layer), the GOx enzymatic layer, the first-permeability selective layer (outer perm-selective layer), or the outer protective layer.

The enzyme GOx may be deposited and trapped onto the surface of the WE wire using some combination of electrodeposition, electro-polymerization, and physical adsorption of a polymer such as o-phenylenediamine, aniline, or other polymer. The inclusion of the polymer may have multiple purposes. For example, the polymerized mesh may physically trap the GOx enzyme and adsorb it to the WE surface. In another example, the polymer backbone may be electrically conductive and facilitate the transfer of electrons to the WE. Additionally or alternatively, other polymer layers constructed of, for example, Nafion, Cellulose acetate, the like or a combination thereof, deposited below or above the GOx deposition layer may normalize the levels of glucose and oxygen. These other polymer layers may help linearize a current response to physiologically relevant glucose concentrations. Additionally or alternatively, the other polymer layers, (such as cellulose acetate) may protect the activated WE metal surface. This protection is beneficial because the activated surface of the WE is important in developing a sensitive glucose sensor because the reaction of the working electrode surface with hydrogen peroxide is primarily responsible for the creation of the electrical signal which is measured by the electrical circuits of the system.

In another example, a sensor may be configured to remove or reduce the CGM's dependence on dissolved oxygen and help substitute the function of oxygen with the use of a small molecule, sometimes referred to as the "mediator". The mediator may function in a similar fashion to oxygen in the context of the sensor system to facilitate the transfer of electrons from the enzyme (GOx) catalytic center to the electrode. The mediator may be fabricated into the sensor head in a proportion that may enable this functionality. In some examples, the proportion may be empirically determined. The mediator may be constructed out of molecules that can accept electrons in a stable manner and/or give up the electrons in certain conditions, such as at the electrode surface. A mediator can include any number of materials, such as ferrocene, ferricyanide, Osmium based transition metal complexes or the like. In some examples, the enzyme (GOx), the mediator(s) and/or polymers may be covalently bound to the metal electrode to form the sensor for detecting glucose. In this sensor configuration, construction may also be encapsulated with multiple layers of polymers (such as Nafion). The layers of polymers may serve specific purposes. Additionally or alternatively, the polymers may limit the concentration of glucose at the enzyme to linearize the current response to various concentrations of glucose. In some examples, the addition of mediators may include additional steps to ensure biocompatibility of the mediator molecules along with the stability of the sensor fabrication to keep the molecules from leeching after invasive implantation. In some examples, an electrode that includes a mediator may be constructed using a of Gold (Au), Pt/Ir, or Pt/Au electrode.

Advantageously, the selected polymer layers and GOx are biocompatible. Similarly, Pt, Au and Ag are noble metals with excellent biocompatibility.

Various methods of recording electrical signal may be used. For example, cyclic voltammometry, amperometry, voltammetry, or another method of recording electrical signal may be used. A method may be selected based on parameters such as reproducibility and accuracy of glucose concentrations over the lifetime of the sensor.

A CGM sensor may detect and convert concentrations of glucose to a proportional electrical signal (current or potential) by a series of electron transfer steps between GOx, FAD, peroxide molecules and finally to the working electrode. However, this proportionality constant is sensitive to a range of physical and biochemical parameters. These parameters may be controlled and standardized during fabrication in order to help produce more consistent signal. For example, such parameters and example (but not exclusive) method(s) of standardizing these parameters for fabrication can include, but are not limited to: 1) geometry and size of the sensor head, which may be evaluated by cyclic voltammometry of a known and well-behaved redox compound like ferrocene or potassium ferrocyanide for consistency; 2)

amount of glucose oxidase enzyme captured on the sensor head, which may be evaluated by electrical signal detected on the working electrode to known concentrations of peroxide and compared with the glucose response; 3) applied voltage between the working electrode and the reference electrode, wherein the working voltage can be determined by cycling through or probing of various voltages for a known concentration of glucose; 4) polymer coating(s) that may normalize the concentration of glucose and oxygen, which can be evaluated based on the linearization of electrical response to glucose concentration with various concentration of polymer coatings; 5) the surface "activation" and preservation of platinum electrode that oxidizes hydrogen peroxide, wherein the inclusion of cellulose acetate polymer coating of working electrode may protect the surface "activation" in a functioning glucose sensor for the purposes of standardization and consistency; 6) the polymer coating that filters out interfering species such as ascorbic acid, urea, acetaminophen, wherein a Nafion polymer coating may be utilized to reduce interference in electrical measurements; 7) the conducting polymer that provides an efficient "pathway" for the electrons to reach the platinum electrode, some polymers such as PANI, PoPD and other polymers that may include conducting polymers may be used for this purpose; 8) the local diffusion behavior of glucose and oxygen near the sensor, wherein the diffusion behavior can be characterized by comparing the electrical response of the constructed sensor to standard equations of electrochemistry; 9) leeching or degradation of polymer layers, mediators and glucose oxidase enzyme, wherein the binding strength of the components of the sensor will be characterized by following the "leakage" of these components during long-term usage and incubation of the sensor in in-vitro buffer or blood/plasma. UV/Vis spectroscopy, chemical determination, Raman spectroscopy and atomic force microscopy are some of the biophysical methods that can be used to characterize this phenomenon; 10) the drift/stability of the reference electrode (Ag/AgCl), wherein the Ag/AgCl reference electrode is constructed with any number of methods and wherein the electrodes may be calibrated against industry leading, low-noise and long-term stable commercial Ag/AgCl electrodes; 11) temperature and pH of the measurement location, which can be accounted for in testing in an electrochemical cell to test for the temperature and pH consistent with the human body (pH 7.4 and 37° C.); 12) depth of penetration of the sensor into the ISF. Ideally, the depth of insertion of the sensor head should be fairly precisely controlled using the applicator. This depth will partially determine the lag time of glucose values between blood and ISF. Location of the CGM (abdomen vs arm) is another factor that determines lag.

When constructing the electrochemical probe, the use of specific metals and electrode surface platting may be used to achieve a desired signal return. Some metals that may be used for this purpose include but are not limited to Platinum, Gold, Silver, and Silver-Chloride. Other combinations of metals and surface platting may also be possible. Other iterations could include other materials, such as electrodes made of carbon nanotubes, graphene electrodes, gold nanoparticles deposited on other metallic surfaces, glassy carbon, Zinc Oxide nanorods, indium tin oxide, the like or a combination thereof.

Once the probe is constructed of the correct combination of metal electrodes, many probe designs also require the application of chemical agents and buffers to either exaggerate or manage the gain of the electro-chemical reaction to target the desired molecule; in this case Glucose.

D. Terminology

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. The terms "comprising," "including," "having," and the like are synonymous and are used inclusively, in an open-ended fashion, and do not exclude additional elements, features, acts, operations, and so forth. That is, the above terms are to be interpreted synonymously with the phrases "having at least" or "including at least." For example, when used in the context of a process, the term "comprising" means that the process includes at least the recited steps, but may include additional steps. When used in the context of a device, the term "comprising" means that the device includes at least the recited features or components, but may also include additional features or components. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conditional language, such as "can," "could," "might," or "may," unless specifically stated otherwise, or otherwise understood within the context as used, is generally intended to convey that certain aspects include, while other aspects do not include, certain features, elements, or steps. Thus, such conditional language is not generally intended to imply that features, elements, or steps are in any way required for one or more aspects or that one or more aspects necessarily include logic for deciding, with or without user input or prompting, whether these features, elements, or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain aspects require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The term "and/or" as used herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The term "temperature independent" as used herein, means that the reading or measurement of the glucose level by the glucose monitoring device or the response of the glucose sensor is not affect or not substantially affected by the change of temperature. In other words, the sensor is insensitive the change of temperature (e.g., change of body temperature as a result of physiological conditions such as hypothermia and hyperpyrexia). In some aspects, the temperature independent property of the glucose monitoring device is maintained within the operating temperature range of the device (e.g., from about 30° C. to about 45° C., from about 33° C. to about 43° C., from about 35° C. to about 41° C., or from about 36° C. to about 40° C. In some aspects, the change of temperature (per ° C.) results in less than 5%, 4%, 3%, 2%, 1%, 0.5%, 0.1% or 0.01% change in the response of the sensor, or the measurement/reading provided by the device, when all the other parameters remain the same (e.g., the glucose concentration is constant).

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. An electrode system for an implantable electrochemical sensor, the electrode system comprising:

a substrate extending from a first end to a second end;

a bilayer working electrode comprising a first continuous layer comprising a first metallic material and a second continuous layer overlaying the first continuous layer, the second continuous layer comprising a second metallic material different from the first metallic material;

a reference electrode, the bilayer working electrode positioned closer to the first end of the substrate than the reference electrode;

a counter electrode; and a plurality of wire parts connecting each of the bilayer working electrode, the reference electrode, and the counter electrode to a plurality of corresponding connector parts positioned proximate the second end of the substrate, wherein the bilayer working electrode and the reference electrode are positioned on a first side of the substrate, and wherein the counter electrode is positioned on a second side of the substrate opposite the first side of the substrate.

2. The electrode system of claim 1, wherein the electrochemical sensor is a glucose sensor.

3. The electrode system of claim 1, wherein the thickness of the first continuous layer is about 2.5-3.5 μm and the thickness of the second continuous layer is about 80-120 Å.

4. The electrode system of claim 1, wherein the reference electrode has a thickness of about 2.5-3.5 μm.

5. The electrode system of claim 1, wherein the counter electrode has a thickness of about 2.5-3.5 μm.

6. The electrode system of claim 1, wherein the substrate comprises two base layers.

7. The electrode system of claim 6, wherein at least one of the two base layers comprises polyimide (PI), polyethylene (PE), or polyethylene terephthalate (PET).

8. The electrode system of claim 1, further comprises a first polymer layer covering part of the bilayer working electrode and the reference electrode.

9. The electrode system of claim 8, wherein the first polymer layer comprises polyimide (PI).

10. The electrode system of claim 8, further comprises a second polymer layer covering part of the counter electrode.

11. The electrode system of claim 10, wherein the second polymer layer comprises polyimide (PI).

12. The electrode system of claim 1, wherein a length of the bilayer working electrode is from 1.3 to 1.5 mm.

13. The electrode system of claim 1, wherein a width of the substrate is about 0.36 mm.

14. The electrode system of claim 1, wherein the first metallic material comprises gold and the second metallic material comprises platinum.

15. The electrode system of claim 1, wherein the counter electrode comprises gold.

16. An implantable glucose sensor comprising:

an electrode system comprising:

a substrate extending from a first end to a second end;

a bilayer working electrode positioned on a first side of the substrate, the bilayer working electrode further comprising:

a first continuous layer comprising gold, the first continuous layer comprising a thickness of about 2.5-3.5 μm;

a second continuous layer comprising platinum, the second continuous layer comprising a thickness of about 80-120 Å;

a reference electrode positioned on the first side of the substrate, the bilayer working electrode positioned closer to the first end of the substrate than the reference electrode;

a counter electrode positioned on a second side of the substrate opposite the first side; and a plurality of wire parts connecting each of the bilayer working electrode, the reference electrode, and the counter electrode to a plurality of corresponding connector parts positioned proximate the second end of the substrate.

17. The glucose sensor of claim 16, wherein the reference electrode comprises silver.

18. The glucose sensor of claim 16, wherein the counter electrode comprises gold.

19. The glucose sensor of claim 16, wherein the reference electrode has a thickness of about 2.5-3.5 μm.

20. The glucose sensor of claim 16, wherein the counter electrode has a thickness of about 2.5-3.5 μm.

* * * * *